US012751693B2

(12) United States Patent
Hattori

(10) Patent No.: US 12,751,693 B2
(45) Date of Patent: Oct. 6, 2026

(54) MEDICAL APPLIANCE

(71) Applicant: FUJIFILM Corporation, Tokyo (JP)

(72) Inventor: Shintaro Hattori, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 180 days.

(21) Appl. No.: 18/674,920

(22) Filed: May 27, 2024

(65) Prior Publication Data

US 2024/0398373 A1 Dec. 5, 2024

(30) Foreign Application Priority Data

Jun. 5, 2023 (JP) ................................ 2023-092317

(51) Int. Cl.
*A61B 8/12* (2006.01)
*A61B 1/005* (2006.01)

(52) U.S. Cl.
CPC ................ *A61B 8/12* (2013.01); *A61B 1/005* (2013.01)

(58) Field of Classification Search
CPC ..... A61B 1/0051; A61B 1/009; A61B 1/0052; A61B 1/005; A61B 1/00066
See application file for complete search history.

(56) References Cited

U.S. PATENT DOCUMENTS

2011/0088498 A1 4/2011 Ettwein et al.
2013/0184528 A1* 7/2013 Onuki .................. A61B 17/062 600/146
2020/0129050 A1* 4/2020 Sinay ................. A61B 1/00128
2020/0196834 A1 6/2020 Tah
2020/0367723 A1* 11/2020 Yoshinaga ............. G02B 23/24
2021/0212556 A1* 7/2021 Nguyen ............. A61B 1/00042
2023/0355082 A1* 11/2023 Carruthers ............. A61B 1/018
2025/0000344 A1* 1/2025 Tomberg .............. A61B 1/0051

FOREIGN PATENT DOCUMENTS

DE 102012012877 1/2014
JP S6254702 4/1987
JP 2008023064 2/2008

OTHER PUBLICATIONS

"Search Report of Europe Counterpart Application", issued on Nov. 7, 2024, p. 1-p. 9.

* cited by examiner

*Primary Examiner* — Michael J Carey
*Assistant Examiner* — Dayton Hyun Jin Barker
(74) *Attorney, Agent, or Firm* — JCIPRNET

(57) ABSTRACT

Provided is a medical appliance with which it is possible to improve usability in relation to a fixing operation and an unfixing operation of a bendable portion.
A disk of which an outer peripheral surface is provided with a serrated portion is provided to be integrally rotatable with a sprocket, a plunger that is transitionable between a locking position where a locking portion is locked at the serrated portion and a non-locking position where the locking portion is not locked at the serrated portion is provided, and a switching operation portion is rotated around a longitudinal axis of an operation portion so that the plunger selectively switches between the locking position and the non-locking position.

11 Claims, 13 Drawing Sheets

MEDICAL APPLIANCE

CROSS-REFERENCE TO RELATED APPLICATION

The present application claims priority under 35 U.S.C § 119(a) to Japanese Patent Application No. 2023-092317 filed on Jun. 5, 2023, which is hereby expressly incorporated by reference, in its entirety, into the present application.

BACKGROUND OF THE INVENTION

1. Field of the Invention

The present invention relates to a medical appliance, and particularly to a medical appliance of which a bendable portion provided at an insertion portion is bent by means of a bending operation member of an operation portion.

2. Description of the Related Art

In the case of an endoscope, which is one of medical appliances, a bending operation lever provided at an operation portion is operated so that a bendable portion of an insertion portion is bent. Accordingly, a distal end portion of the insertion portion can be caused to face a desired direction. In addition, there is an endoscope provided with a lock mechanism that locks a bending operation lever not to be operated or unlocks the bending operation lever, so that a bendable portion is fixed in a desired bent state or is unfixed (refer to JP2008-23064A and JP1987-54702U (JP-S62-54702U)).

Disclosed in JP2008-23064A is an endoscope including a bending operation lever that rotates a pulley around which a wire for a bending operation is wound and a lock mechanism that locks the bending operation lever not to be operated. The above-described lock mechanism includes a lock lever, an eccentric lock plate that rotates together with the lock lever, and a locking tapered ring that is provided at a pulley rotary shaft and that abuts the lock plate.

According to JP2008-23064A, in a case where the lock plate is pressed against the locking tapered ring as the lock lever is operated in one direction, the bending operation lever is locked not to be operated. In addition, in a case where the lock plate is withdrawn from the locking tapered ring as the lock lever is operated in the other direction, the bending operation lever is unlocked so that the bending operation lever can be freely operated.

Disclosed in JP1987-54702U (JP-S62-54702U) is an endoscope including an operation knob for a bending operation of a bendable portion and a lock mechanism (means) that locks the operation knob not to be operated. The above-described lock mechanism includes a ratchet gear, a pair of claw members that mesh with the ratchet gear, one of which allows rightward rotation, and the other of which the other allows leftward rotation, and an unlocking member that separates the one of the claw members from the ratchet gear as the operation knob is rotated in one direction and that separates the other of the claw members from the ratchet gear as the operation knob is rotated in the other direction.

According to JP1987-54702U (JP-S62-54702U), in the case of operation stoppage, the pair of claw members and the ratchet gear mesh with each other so that the operation knob is automatically locked not to be operated. In addition, during an operation, the unlocking member makes the operation knob operatable. In addition, in a case where the operation knob is lowered, the pair of claw members and the ratchet gear meshing with each other are completely released from each other, so that the operation knob can be freely operated.

SUMMARY OF THE INVENTION

However, in the case of a technique disclosed in JP2008-23064A, the lock lever needs to be operated in both of a case where the bending operation lever is to be locked not to be operated and a case where the bending operation lever is to be made freely operatable. Therefore, there is a problem that usability for an operator is poor.

However, in the case of a technique disclosed in JP1987-54702U (JP-S62-54702U), the operation knob is automatically locked not to be operated in the case of operation stoppage of the operation knob. Therefore, there is an advantage that usability is better than that in JP2008-23064A described above.

However, according to JP1987-54702U (JP-S62-54702U), an operation of lowering the operation knob, which is complicated, needs to be performed in a case where the operation knob is to be made freely operatable. Therefore, there is a problem that usability for a practitioner is poor as with JP2008-23064A.

The present invention has been made in consideration of such circumstances, and an object thereof is to provide a medical appliance with which it is possible to improve usability in relation to a fixing operation and an unfixing operation of a bendable portion.

A medical appliance according to a first aspect of the present invention includes an insertion portion that includes a bendable portion that is bendable, an operation portion that is connected to a base end side of the insertion portion and that includes a bending operation member, a rotary driving body that is disposed in the operation portion and is rotationally driven by the bending operation member, a bending operation wire that is inserted into the insertion portion and the operation portion and that bends the bendable portion by moving forward and backward in accordance with movement of the rotary driving body, a rotary member that is integrally rotatable with the rotary driving body and of which an outer peripheral surface is provided with an unevenness portion, a locking portion main body that includes a locking portion lockable at the unevenness portion and that is transitionable between a locking position where the locking portion is locked at the unevenness portion and a non-locking position where the locking portion is not locked at the unevenness portion, and a switching operation portion that is provided to be rotatable around a longitudinal axis of the operation portion and that causes the locking portion main body to selectively switch between the locking position and the non-locking position.

A second aspect of the present invention provides the medical appliance according to the first aspect in which, the switching operation portion preferably includes a switching plate that rotates around the longitudinal axis, the switching plate preferably includes a first abutting surface and a second abutting surface that are disposed at different positions in a circumferential direction on a surface of the switching plate that is on a rotary member side, the first abutting surface is preferably provided at a position where a distance to the rotary member is smaller than a distance between the second abutting surface and the rotary member, and the locking portion main body is preferably disposed at the locking position in a case where the locking portion main body abuts the first abutting surface and is preferably disposed at the non-locking position in a case where the locking portion main body abuts the second abutting surface.

A third aspect of the present invention provides the medical appliance according to the second aspect in which, the switching plate preferably includes a third abutting surface that is disposed at a position different from positions of the first abutting surface and the second abutting surface in the circumferential direction on the surface of the switching plate that is on the rotary member side, the third abutting surface is preferably provided at a position where a distance to the rotary member is smaller than a distance between the first abutting surface and the rotary member, and the rotary member preferably enters a state of being not rotatable in a case where the locking portion main body abuts the third abutting surface.

A fourth aspect of the present invention provides the medical appliance according to the second or third aspect in which, the locking portion main body preferably includes a second biasing member that biases the locking portion main body toward a switching plate side.

A fifth aspect of the present invention provides the medical appliance according to any one of the second to fourth aspects in which, the locking portion main body preferably includes a roll body that rotates with the roll body being in contact with the surface of the switching plate that is on the rotary member side.

A sixth aspect of the present invention provides the medical appliance according to any one of the first to fifth aspects in which, the locking portion main body preferably includes the locking portion that is provided on a rotary member side and that has a ball-like shape, and a first biasing member that biases the locking portion toward the rotary member side.

A seventh aspect of the present invention provides the medical appliance according to the fourth aspect in which, the first biasing member preferably has a biasing force that allows the locking portion to climb over the unevenness portion in a case where the rotary member rotates in a state where the locking portion main body is positioned at the locking position.

An eighth aspect of the present invention provides the medical appliance according to any one of the first to seventh aspects in which the rotary driving body is preferably a sprocket.

A ninth aspect of the present invention provides the medical appliance according to any one of the first to seventh aspects in which the rotary driving body is preferably a pulley.

A tenth aspect of the present invention provides the medical appliance according to any one of the first to seventh aspects in which the rotary driving body is preferably a pinion.

An eleventh aspect of the present invention provides the medical appliance according to any one of the first to tenth aspects in which, the rotary driving body and the rotary member are preferably integrated with each other.

A twelfth aspect of the present invention provides the medical appliance according to any one of the first to eleventh aspects in which, the unevenness portions are preferably provided at constant pitches at the outer peripheral surface of the rotary member.

A thirteenth aspect of the present invention provides the medical appliance according to any one of the first to twelfth aspects in which, a pair of the rotary driving bodies, a pair of the rotary members, and a pair of the locking portion main bodies are preferably provided, and the switching operation portion preferably causes at least one of the pair of locking portion main bodies to selectively switch between the locking position and the non-locking position.

According to the aspects of the present invention, it is possible to improve usability in relation to a fixing operation and an unfixing operation of a bendable portion.

DESCRIPTION OF THE PREFERRED EMBODIMENTS

Hereinafter, a medical appliance according to an embodiment of the present invention will be described with reference to the accompanying drawings.

Figure 1:
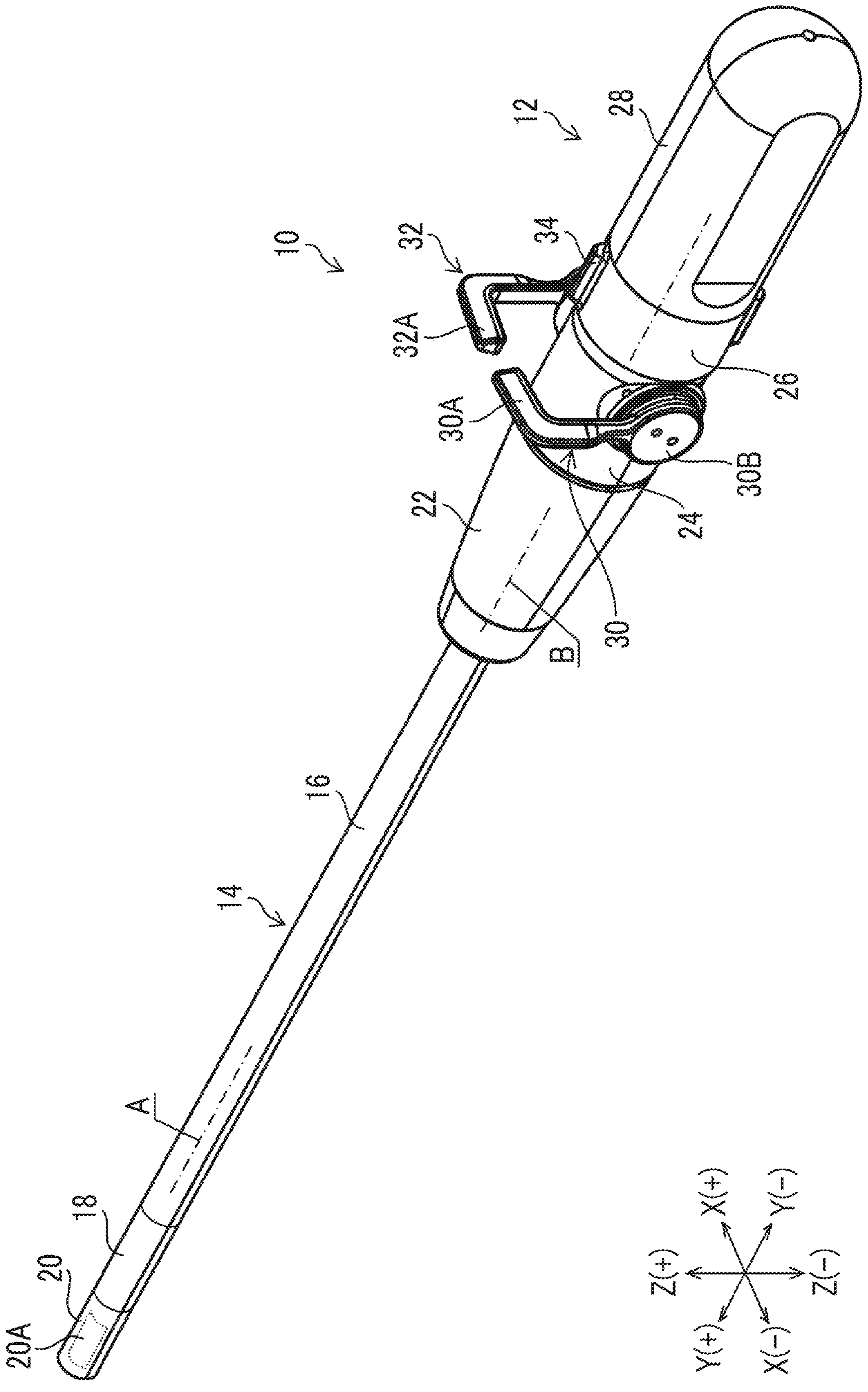
FIG. 1 is an overall perspective view of an ultrasound probe according to an embodiment.

FIG. 1 is an overall perspective view of an ultrasound probe 10 according to an embodiment to which a medical appliance according to the embodiment of the present invention is applied.

Hereinafter, in description of the configuration of each part of the ultrasound probe 10, an XYZ three-dimensional rectangular coordinate system will be used for the sake of convenience of description. In the drawings, a Z direction is a vertical direction, a Z (+) direction is an upward direction, and a Z (−) direction is a downward direction. In addition, an X direction in the drawings is a lateral direction perpendicular to the Z direction, an X (+) direction is a rightward direction, and an X (−) direction is a leftward direction. In addition, a Y direction in the drawings is a direction perpendicular to both of the Z direction and the X direction, a Y (+) direction is a direction toward a distal end, and a Y (−) direction is a direction toward a base end. Note that each of the above-described directions is a direction related to a case where an operation portion 12 of the ultrasound probe 10 is gripped by an operator and the ultrasound probe 10 is seen from above by the operator.

As shown in FIG. 1, the ultrasound probe 10 includes a tubular insertion portion 14 of which a longitudinal axis A extends along the Y direction and the tubular operation portion 12 that is connected to a base end side (on a side to which the Y (−) direction extends) of the insertion portion 14.

The insertion portion 14 includes an insertion portion main body 16, a bendable portion 18 that is provided at a distal end side (on a side to which the Y (+) direction extends) of the insertion portion main body 16, and a probe 20 that is provided at a distal end side of the bendable portion 18. The insertion portion main body 16 of the present example is rigid. The insertion portion 14 and the operation portion 12 are examples of an insertion portion and an operation portion according to the embodiment of the present invention.

The bendable portion 18 is configured to be bendable, for example, by consecutively installing a plurality of ring-shaped bending pieces along the longitudinal axis A and is bent in the lateral direction (the X direction) and the vertical direction (the Z direction) in the case of forward and backward movement of a bending operation wire, which will be described later.

The probe 20 is a linear type probe of which an ultrasonic wave emission surface 20A is formed to be flat, and the probe 20 includes a plurality of oscillators that transmit and receive ultrasonic waves to and from an imaging target portion (an organ (for example, a liver)) of a subject. The probe 20 is connected to an ultrasound imaging apparatus (not shown) through a wiring line inserted into the insertion portion 14 and the operation portion 12. The probe 20 is not limited to a linear type probe, and may be a convex type or radial type probe.

Figure 2:
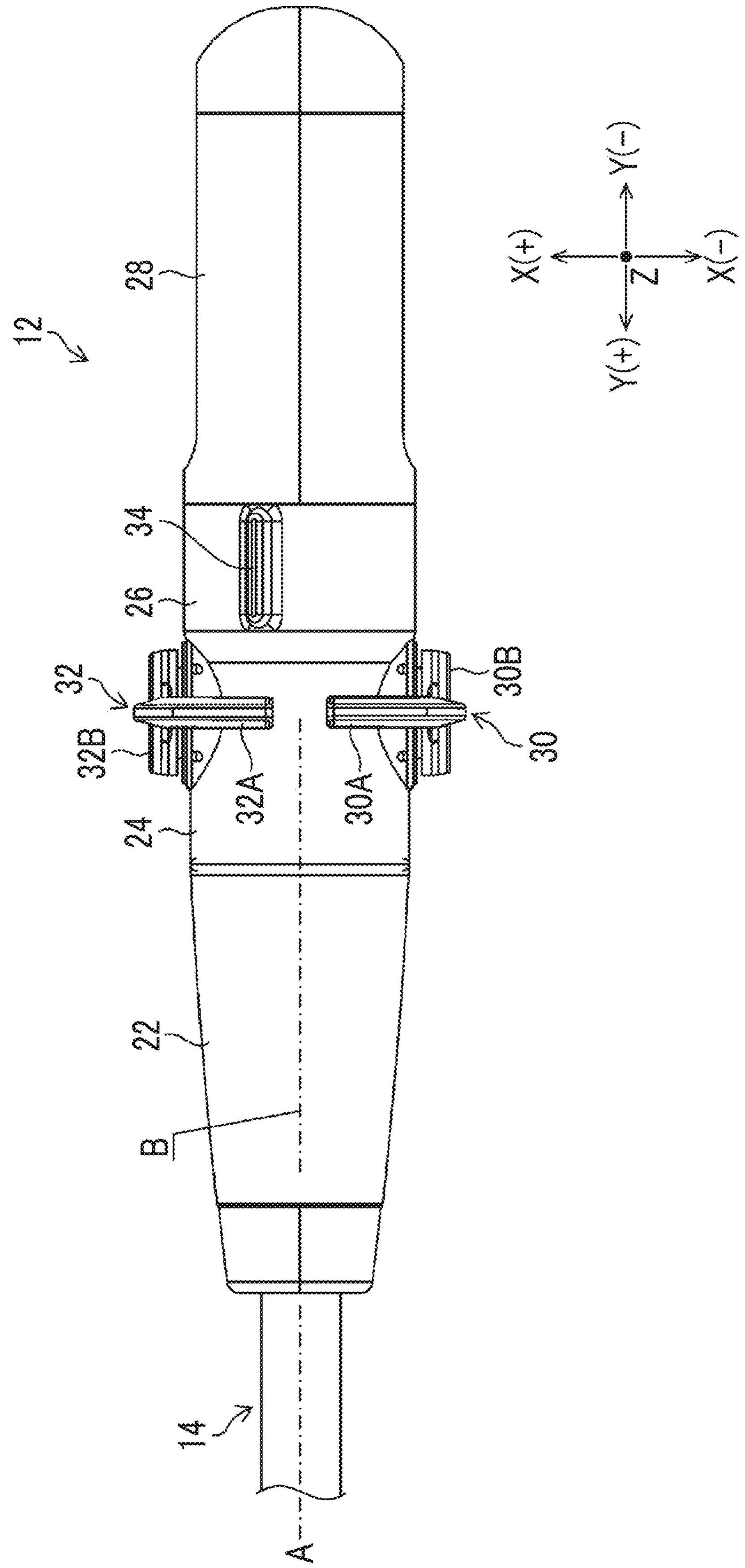
FIG. 2 is a top view showing an operation portion of the ultrasound probe as seen from an upper side.

FIG. 2 is a top view showing the operation portion 12 of the ultrasound probe 10 as seen from an upper side (a side to which the Z (+) direction extends). As shown in FIGS. 1 and 2, a longitudinal axis B of the operation portion 12 extends along the longitudinal axis A of the insertion portion 14 and the operation portion 12 includes a connecting portion 22, a lever attachment portion 24, a switching operation portion 26, and a grip portion 28, which are arranged in this order in a direction from a distal end side (a side to which the Y (+) direction extends) to a base end side (a side to which the Y (−) direction extends) along the longitudinal axis B.

A base end portion of the insertion portion main body 16 is connected to the connecting portion 22. A lateral bending lever 30 and a vertical bending lever 32, which are bending operation members, are swingably attached to the lever attachment portion 24.

The switching operation portion 26 is formed in a ring-like shape and is provided to be rotatable around the longitudinal axis B with respect to the connecting portion 22, the lever attachment portion 24, and the grip portion 28 which are not rotatable. In addition, regarding the switching operation portion 26, a distal end side and a base end side of the switching operation portion 26 are rotatably connected to the lever attachment portion 24 and the grip portion 28 via airtight seals (for example, O-rings (not shown)), respectively. In addition, a portion of an outer peripheral surface of the switching operation portion 26 is provided with a finger hook portion 34, which is a linear protrusion extending along the Y direction.

The grip portion 28 is a portion that is gripped by the right palm or the left palm of the operator. The operator can insert or remove the insertion portion 14 into or from the body of a subject while gripping the grip portion 28 and can operate the lateral bending lever 30, the vertical bending lever 32, and the switching operation portion 26 by using, for example, a thumb.

The lateral bending lever 30 and the vertical bending lever 32 are disposed at positions that are 180 degrees offset from each other in a circumferential direction of the lever attachment portion 24, and are formed in L-like shapes that are line-symmetrical with respect to the longitudinal axis B. Note that in a case where the lateral bending lever 30 and the vertical bending lever 32 are viewed from a side to which the Z (+) direction extends, upper end portions 30A and 32A of the lateral bending lever 30 and the vertical bending lever 32 are disposed along the X direction. The operator can perform a swing operation of the lateral bending lever 30 and the vertical bending lever 32 in a state where the ball of a thumb is put on the upper end portions 30A and 32A.

Bending Operation Mechanism

Next, a bending operation mechanism for a bending operation of the bendable portion 18 will be described.

Figure 3:
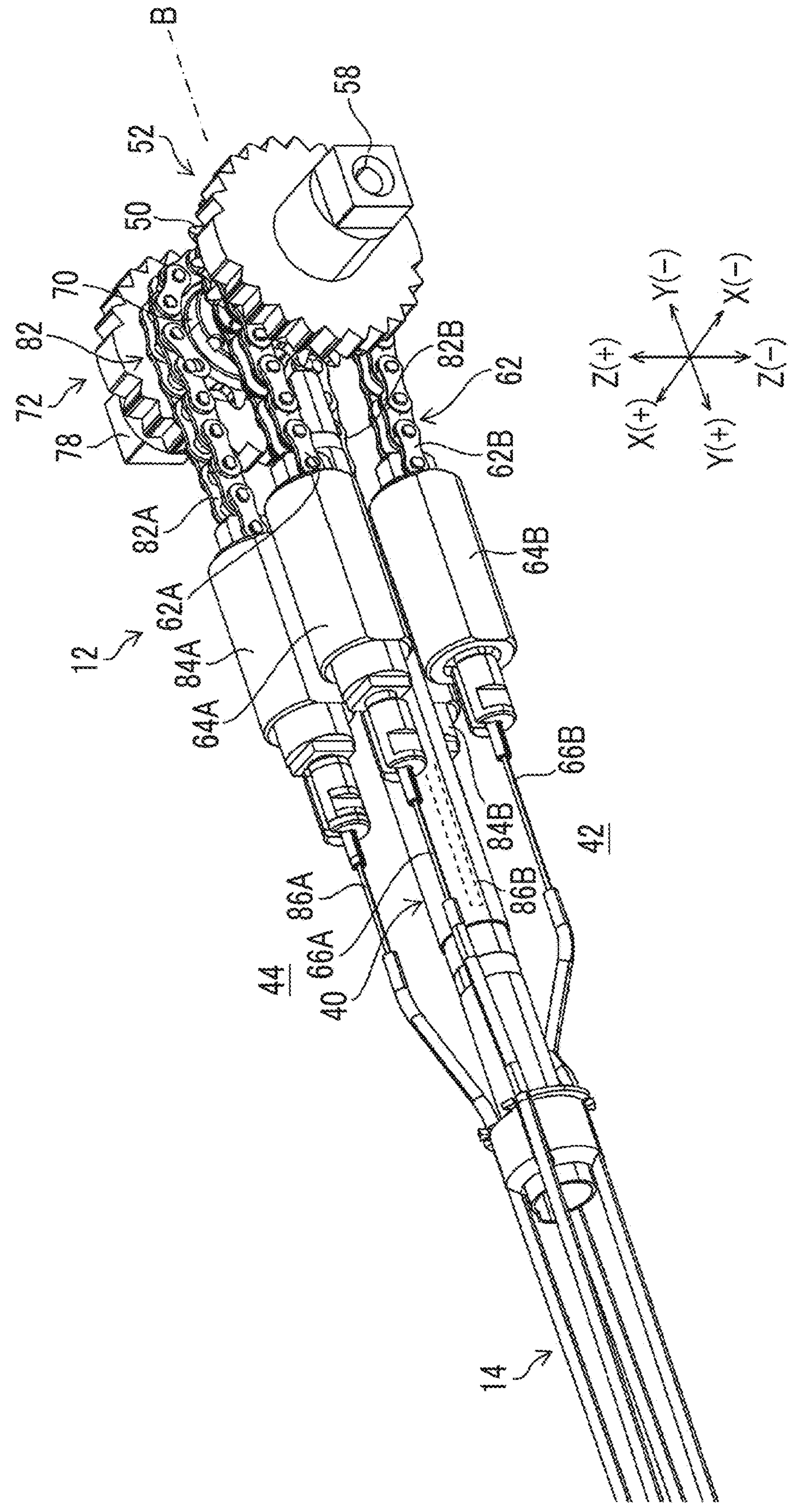
FIG. 3 is a perspective view showing a configuration of a bending operation mechanism.
Figure 4:
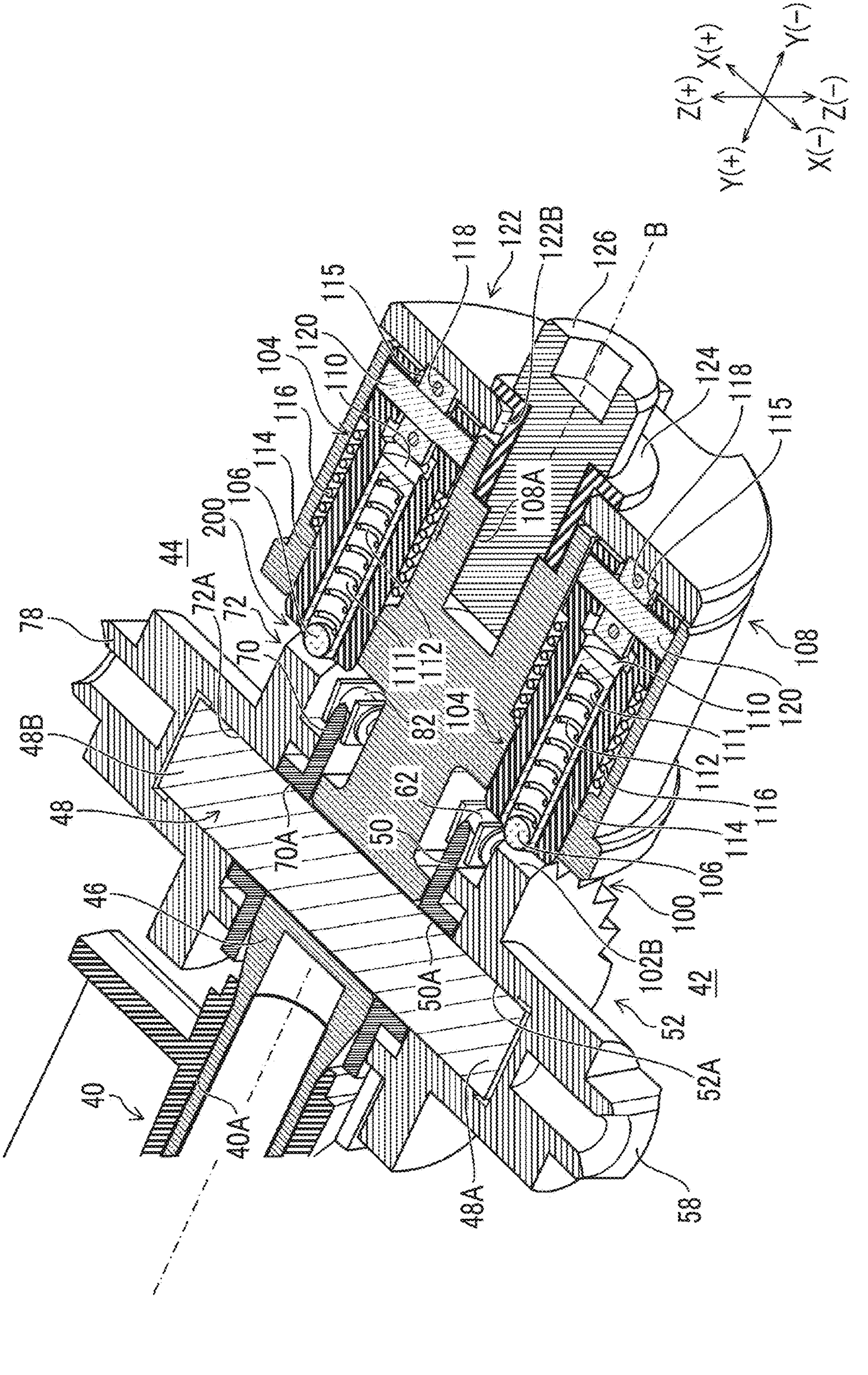
FIG. 4 is a cross-sectional view of a portion of the bending operation mechanism which is taken along an XY plane perpendicular to a Z direction.

FIG. 3 is a perspective view showing a configuration of the bending operation mechanism. FIG. 4 is a cross-sectional view of a portion of the bending operation mechanism which is taken along an XY plane perpendicular to the Z direction. In addition, FIG. 5 is a cross-sectional view of a portion of the bending operation mechanism which is taken along an XZ plane perpendicular to the Y direction.

Figure 5:
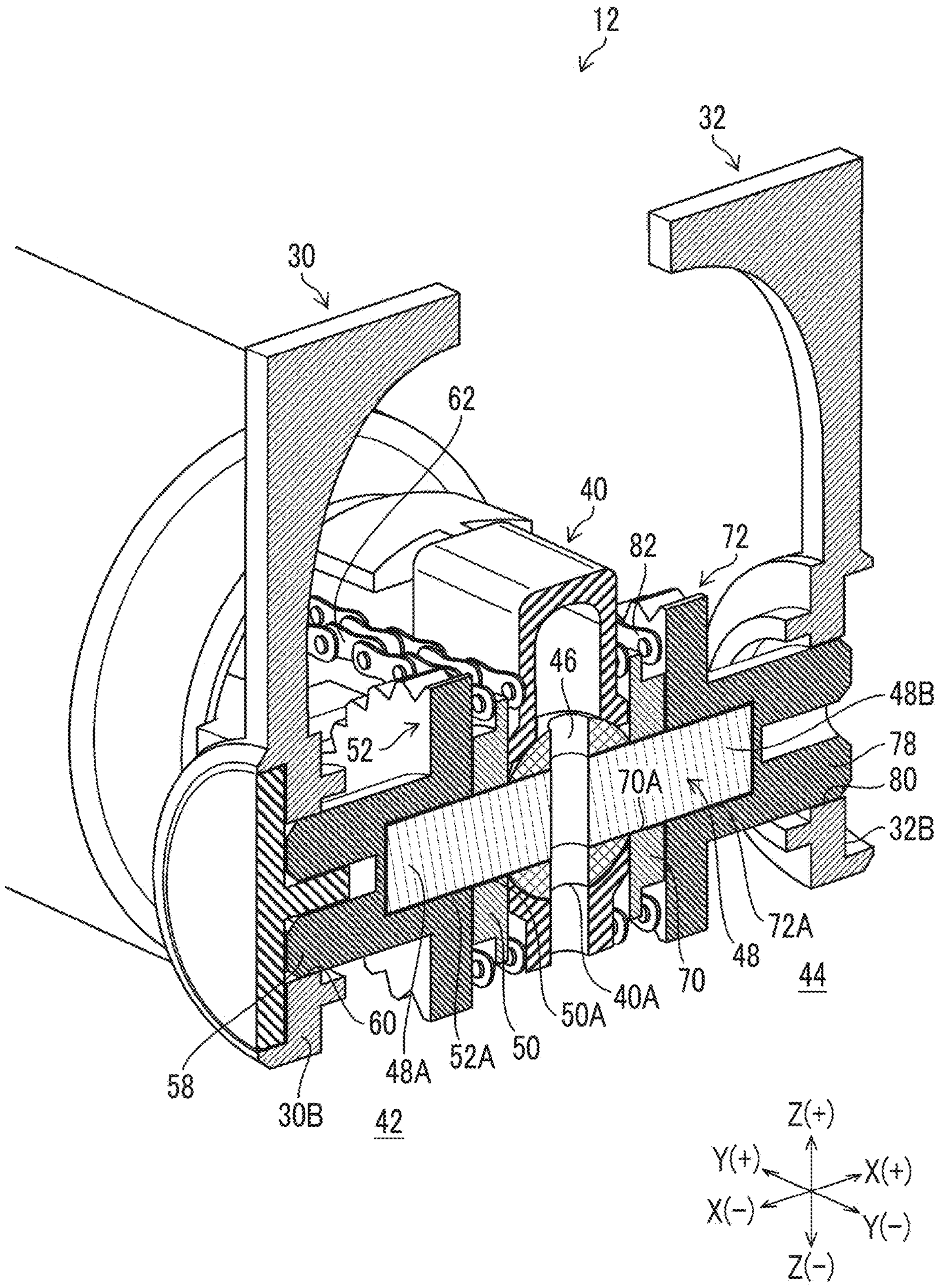
FIG. 5 is a cross-sectional view of a portion of the bending operation mechanism which is taken along an XZ plane perpendicular to a Y direction.

As shown in FIGS. 3 to 5, a tubular body 40 is provided inside the operation portion 12 along the longitudinal axis B and a pair of operation regions 42 and 44 is provided on both sides of the tubular body 40 in the X direction.

A shaft supporting portion 46 (refer to FIG. 4) disposed along the longitudinal axis B is attachably and detachably attached to a base end opening portion 40A of the tubular body 40. A shaft 48, which serves as a supporting shaft for sprockets 50 and 70 (which will be described later), is fixed to the shaft supporting portion 46 in a penetrating manner. The shaft 48 is disposed along the X direction, one end portion 48A is disposed on the operation region 42 side and the other end portion 48B is disposed on the operation region 44 side.

The above-described sprockets 50 and 70 are mounted on the one end portion 48A and the other end portion 48B of the shaft 48, respectively, and the sprockets 50 and 70 are attached to be rotatable with respect to the shaft 48. Hereinafter, detailed description will be provided.

The sprocket 50 (refer to FIGS. 4 and 5) is mounted to be rotatable with respect to the shaft 48 with a bearing hole 50A of the sprocket 50 mounted onto the one end portion 48A of the shaft 48. In addition, a disk 52 is disposed, with respect to the sprocket 50, on a side to which the X (−) direction extends. The disk 52 is mounted to be rotatable with respect to the shaft 48 with a bearing hole 52A of the disk 52 mounted onto the one end portion 48A penetrating the bearing hole 50A.

Figure 6:
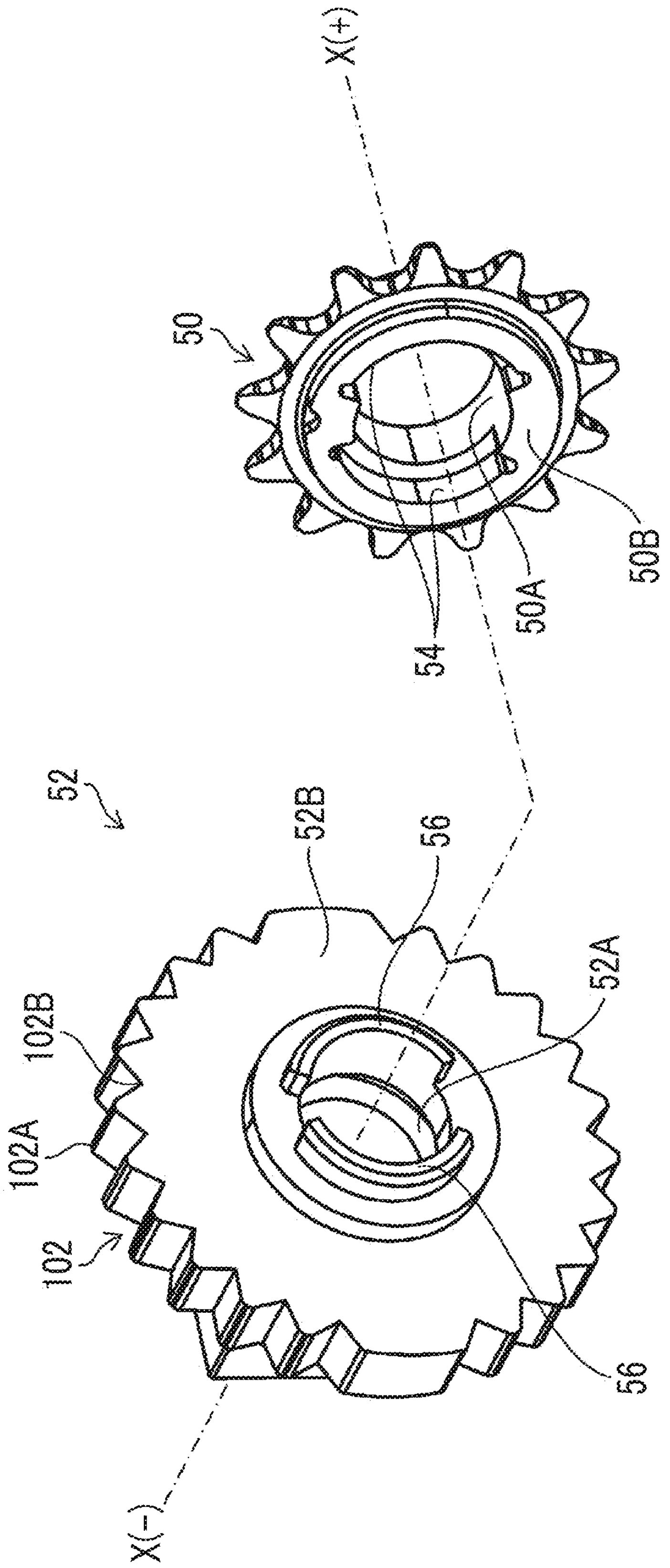
FIG. 6 is a perspective view showing a connection structure between a sprocket and a disk.

FIG. 6 is an assembly view showing the sprocket 50 and the disk 52 separated from each other. As shown in FIG. 6, the sprocket 50 and the disk 52 are connected to each other in a case where a pair of arc-shaped recess portions 54 and a pair of arc-shaped protrusion portions 56, which are respectively formed at facing surfaces 50B and 52B of the sprocket 50 and the disk 52, are engaged with each other. Accordingly, the sprocket 50 and the disk 52 are integrally rotated with respect to the shaft 48.

As shown in FIG. 5, the lateral bending lever 30 is disposed, with respect to the disk 52, on the side to which the X (−) direction extends. The lateral bending lever 30 and the disk 52 are connected to each other in a case where a hole portion 60 formed at a circular base portion 30B of the lateral bending lever 30 is fitted to a protrusion portion 58 of the disk 52 that protrudes toward the side to which the X (−) direction extends. With such a connection configuration, the lateral bending lever 30 is configured to be swingable around the shaft 48. In addition, in a case where the lateral bending lever 30 is operated to swing by the operator, the sprocket 50 and the disk 52 are integrally rotationally driven in the same direction by the lateral bending lever 30.

A chain 62 (refer to FIG. 3) is wound around the sprocket 50. Base end portions of a pair of wires 66A and 66B are connected to one end portion 62A and the other end portion 62B of the chain 62 via connection tools 64A and 64B, respectively. The pair of wires 66A and 66B is inserted into the operation portion 12 and the insertion portion 14 of FIG. 1, and distal end portions thereof are fixed to a pair of fixation ends (not shown) for a lateral bend, the fixation ends being provided in the bendable portion 18. The fixation ends are provided at positions that are 180 degrees offset from each other in a circumferential direction of an inner surface of the bendable portion 18.

The sprocket 70 (refer to FIGS. 4 and 5) is mounted to be rotatable with respect to the shaft 48 with a bearing hole 70A of the sprocket 70 mounted onto the other end portion 48B of the shaft 48. In addition, a disk 72 is disposed, with respect to the sprocket 70, on a side to which the X (+) direction extends. The disk 72 is mounted to be rotatable with respect to the shaft 48 with a bearing hole 72A of the disk 72 mounted onto the other end portion 48B penetrating the bearing hole 70A.

The sprocket 70 and the disk 72 are connected to each other by means of the same engagement structure (an engagement structure formed by the pair of arc-shaped recess portions 54 and the pair of arc-shaped protrusion portions 56) as an engagement structure shown in FIG. 6. Accordingly, the sprocket 70 and the disk 72 are integrally rotated with respect to the shaft 48. Note that the engagement structure of the sprocket 70 and the disk 72 is the same as the engagement structure shown in FIG. 6 as described above and thus the engagement structure is not shown in the drawings.

As shown in FIG. 5, the vertical bending lever 32 is disposed, with respect to the disk 72, on the side to which the X (+) direction extends. The vertical bending lever 32 and the disk 72 are connected to each other in a case where a hole portion 80 formed at a circular base portion 32B of the vertical bending lever 32 is fitted to a protrusion portion 78 of the disk 72 that protrudes toward the side to which the X (+) direction extends. With such a connection configuration, the vertical bending lever 32 is configured to be swingable around the shaft 48. In addition, in a case where the vertical bending lever 32 is operated to swing by the operator, the sprocket 70 and the disk 72 are integrally rotationally driven in the same direction by the vertical bending lever 32.

A chain 82 (see FIG. 3) is wound around the sprocket 70. Base end portions of a pair of wires 86A and 86B are connected to one end portion 82A and the other end portion 82B of the chain 82 via connection tools 84A and 84B, respectively. The pair of wires 86A and 86B is inserted into the operation portion 12 and the insertion portion 14 of FIG. 1, and distal end portions thereof are fixed to a pair of fixation ends (not shown) for a vertical bend, the fixation ends being provided in the bendable portion 18. The fixation ends are fixed to positions that are 180 degrees offset from each other in the circumferential direction of the inner surface of the bendable portion 18 and are provided at positions 90 degrees offset from the above-described pair of fixation ends for the lateral bend, respectively.

According to the bending operation mechanism configured as described above, in a case where the lateral bending lever 30 is swung, the sprocket 50 is rotationally driven, one of the pair of wires 66A and 66B is pulled to a side to which the Y (−) direction extends via the chain 62 in accordance with the rotation of the sprocket 50, and the other of the wires 66A and 66B is drawn out. Accordingly, the bendable portion 18 is bent in the lateral direction.

Similarly, in a case where the vertical bending lever 32 is swung, the sprocket 70 is rotationally driven, one of the pair of wires 86A and 86B is pulled to a side to which the Y (−) direction extends via the chain 82 in accordance with the rotation of the sprocket 70, and the other of the wires 86A and 86B is drawn out. Accordingly, the bendable portion 18 is bent in the vertical direction.

Note that each of the sprockets 50 and 70 is an example of a rotary driving body according to the embodiment of the present invention. In addition, each of the pair of wires 66A and 66B and the pair of wires 86A and 86B is an example of a bending operation wire according to the embodiment of the present invention.

Lock Mechanism

Next, a lock mechanism used to fix the bendable portion 18 in a desired bent state and to unfix the bendable portion 18 will be described. In the embodiment, as shown in FIG. 4, a pair of lock mechanisms 100 and 200 for a lateral bend and a vertical bend is provided as the lock mechanism. The lock mechanism 100 is disposed on the operation region 42 side and the lock mechanism 200 is disposed on the operation region 44 side.

Since the lock mechanisms 100 and 200 of the present example have the same configuration as each other, the lock mechanism 100 for a lateral bend will be mainly described here. Note that regarding the lock mechanism 200 for a vertical bend, description may be omitted with the same reference numerals given to the same members as those of the lock mechanism 100 or members similar to those of the lock mechanism 100.

The lock mechanism 100 includes the disk 52, a plunger 104, and the switching operation portion 26 (refer to FIG. 1). Note that the switching operation portion 26 is shared with the lock mechanism 200.

The disk 52 can be rotated integrally with the sprocket 50 as described above. As shown in FIG. 6, an outer peripheral surface of the disk 52 is provided with a serrated portion 102 at which unevenness portions including tooth tips 102A and tooth grooves 102B are formed at constant pitches.

Here, the unevenness portion means a portion at which bulge portions (tooth tips 102A) and depression portions (tooth grooves 102B) are consecutively formed in a circumferential direction at the outer peripheral surface of the disk 52. In this case, a difference in height (the radius of a circumscribed circle of the tooth tips 102B—the radius of an inscribed circle of the tooth grooves 102B) between the tooth tips 102A which are protrusion portions and the tooth grooves 102B which are recess portions and the pitch of the unevenness portions are appropriately determined based on a relationship between the size (the diameter) of a locking portion 106 (which will be described later) and a biasing force of a spring 112, in accordance with required accuracy with respect to a latched state (which will be described later). The constant pitch of the unevenness portions means not only a strictly constant pitch but also an approximately constant pitch. That is, for example, the constant pitch includes a processing error that occurs in a case where the tooth tips 102A and the tooth grooves 102B of the serrated portion 102 are processed. The disk 52 is an example of a rotary member according to the embodiment of the present invention.

As shown in FIG. 4, the plunger 104 includes the locking portion 106 that is lockable at the serrated portion 102 (the tooth groove 102B side). In addition, the plunger 104 is configured to be able to perform a three-stage transition between a locking position (refer to FIG. 9A) where the locking portion 106 is locked at the serrated portion 102, a non-locking position (refer to FIG. 9B) where the locking portion 106 is not locked at the serrated portion 102, and a lock position (refer to FIG. 9C) where the plunger 104 is pressed against the serrated portion 102 to a greater degree than that in the case of the locking position. Switching between the locking position, the non-locking position, and the lock position of the plunger 104 is selectively performed by means of the switching operation portion 26. First, the plunger 104 will be described. Note that the description of FIGS. 9A to 9C will be made later.

The plunger 104 is mounted in a plunger supporting portion 108. The plunger 104 includes a locking pin 110 that is disposed along the Y direction, the locking portion 106 that is provided on the disk 52 side (the side to which the Y (+) direction extends) with respect to the locking pin 110, the spring 112 that biases the locking portion 106 toward the disk 52 side with respect to the locking pin 110, a tubular sleeve 114 that holds the locking pin 110 and is movable along the Y direction together with the locking pin 110, a spring 116 that biases the locking pin 110 toward a switching plate 122 (which will be described later) side (the side to which the Y (–) direction extends) together with the sleeve 114, and a rolling body 118 that is rotatably provided in a base end opening portion 115 of the sleeve 114.

Here, the plungers 104 of the pair of lock mechanisms 100 and 200 are disposed at positions that are 180 degrees offset from each other in a circumferential direction of the plunger supporting portion 108. The plunger supporting portion 108 includes the above-described shaft supporting portion 46 provided on a distal end side thereof. That is, the plunger supporting portion 108 is attachably and detachably attached to the tubular body 40 via the shaft supporting portion 46.

The locking portion 106 is formed in a ball-like shape. In addition, inside the locking pin 110, a spring accommodation groove 111, in which the spring 112 can be accommodated, is provided along an axial direction (the Y direction) of the locking pin 110. The spring accommodation groove 111 is open on a distal end side of the locking pin 110, and the locking portion 106 is disposed at an opening portion (a distal end portion of the locking pin 110) of the spring accommodation groove 111. The spring 112 that biases the locking portion 106 toward the disk 52 side is disposed in the spring accommodation groove 111. Note that the plunger 104 and the locking portion 106 correspond to a locking portion main body and a locking portion according to the embodiment of the present invention.

The locking pin 110 is fixed inside the sleeve 114. The sleeve 114 is disposed by being inserted into the spring 116 that is mounted in the plunger supporting portion 108 along the Y direction, and the sleeve 114 is biased toward the switching plate 122 by a biasing force of the spring 116.

The rolling body 118 is rotatably attached to the base end opening portions 115 of the sleeve 114 via a shaft 120 (refer to FIGS. 4 and 9) disposed along the X direction. Regarding the rolling body 118, the base end opening portions 115 accommodates not the entire rolling body 118 and a portion (a portion that is closer to the side to which the Y (–) direction extends than the shaft 120 is) of the rolling body 118 that is on a base end side is disposed to protrude from a base end surface 115A of the sleeve 114 to the side to which the Y (–) direction extends. Such a portion (hereinafter, referred to as an abutting portion 118A) is pressed, by the biasing force of the spring 116, against a surface 122A (refer to FIGS. 9A to 9C (hereinafter, referred to as a front surface 122A)) of the switching plate 122 that is on the disk 52 side.

In a case where the switching plate 122 is rotated around the longitudinal axis B as described later in a state where the abutting portion 118A is pressed against the front surface 122A, the rolling body 118 rotates around the shaft 120 due to frictional resistance between the abutting portion 118A and the front surface 122A. Accordingly, the switching plate 122 is smoothly rotated. Note that the rolling body 118 is an example of a roll body according to the embodiment of the present invention and is composed of, for example, a miniature bearing.

As shown in FIGS. 1 and 2, the switching operation portion 26 is a portion on which a switching operation, which is performed to selectively switch the position of the plunger 104 between the above-described three positions (the locking position, the non-locking position, and the lock position), is performed.

The switching operation portion 26 is provided to be rotatable around the longitudinal axis B of the operation portion 12. Specifically, the switching operation portion 26 includes a ring-shaped operation ring 121 (refer to FIG. 7) constituting an outer peripheral portion of the operation portion 12, the switching operation is performed on the operation ring 121, and the operation ring 121 is provided to be rotatable around the longitudinal axis B of the operation portion 12. In addition, the switching operation portion 26 includes the switching plate 122 that rotates around the longitudinal axis B (refer to FIG. 4). Note that the switching operation portion 26 and the switching plate 122 are examples of a switching operation portion and a switching plate according to the embodiment of the present invention.

As shown in FIG. 4, the switching plate 122 is disposed on a base end side (the side to which the Y (–) direction extends) with respect to the plunger supporting portion 108. In addition, a bush 124 is mounted in a bearing hole 122B of the switching plate 122 and the bush 124 is fixed to a screw hole 108A of the plunger supporting portion 108. Accordingly, the switching plate 122 is rotatably attached to the plunger supporting portion 108 via the bush 124. In addition, the screw hole 108A is formed along the longitudinal axis B. Accordingly, the switching plate 122 is rotatable around the longitudinal axis B with respect to the plunger supporting portion 108. Furthermore, a bolt 126 screwed into the screw hole 108A via the bush 124 prevents the switching plate 122 from falling off the plunger supporting portion 108.

Figure 7:
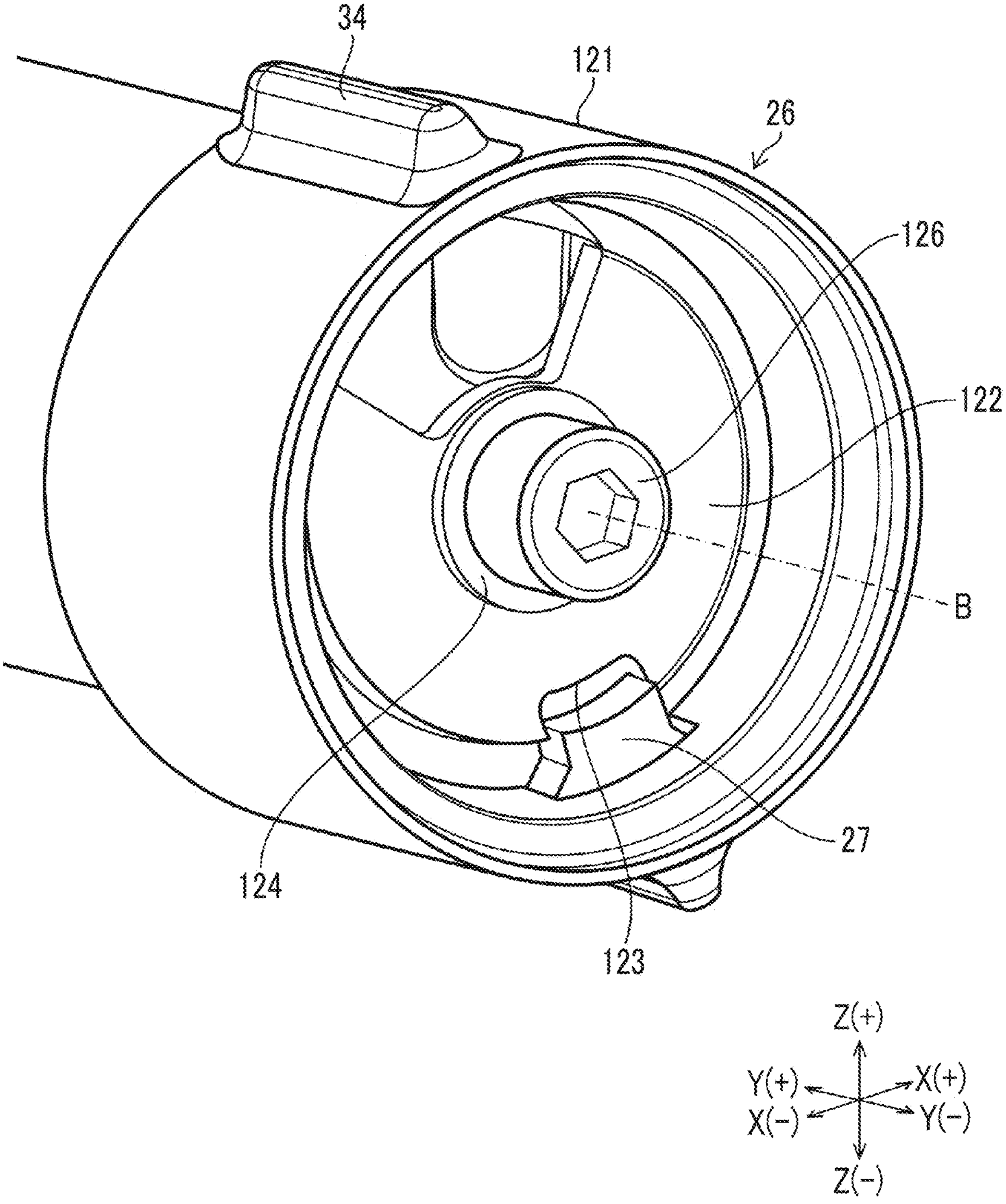
FIG. 7 is a perspective view showing a connection structure between an operation ring and a switching plate.

FIG. 7 is a perspective view of a connection structure between the operation ring 121 and the switching plate 122 and is a perspective view as seen from the side to which the Y (–) direction extends. As shown in FIG. 7, a protrusion portion 27 is formed at an inner peripheral surface of the operation ring 121, a recess portion 123 is formed at an outer peripheral portion of the switching plate 122, and the operation ring 121 and the switching plate 122 are integrally connected to each other with the protrusion portion 27 and the recess portion 123 engaged with each other. Accordingly, in a case where the operation ring 121 of the switching operation portion 26 is operated to be rotated around the longitudinal axis B, the switching plate 122 and the operation ring 121 are integrally rotationally driven in the same direction as each other.

Figure 8:
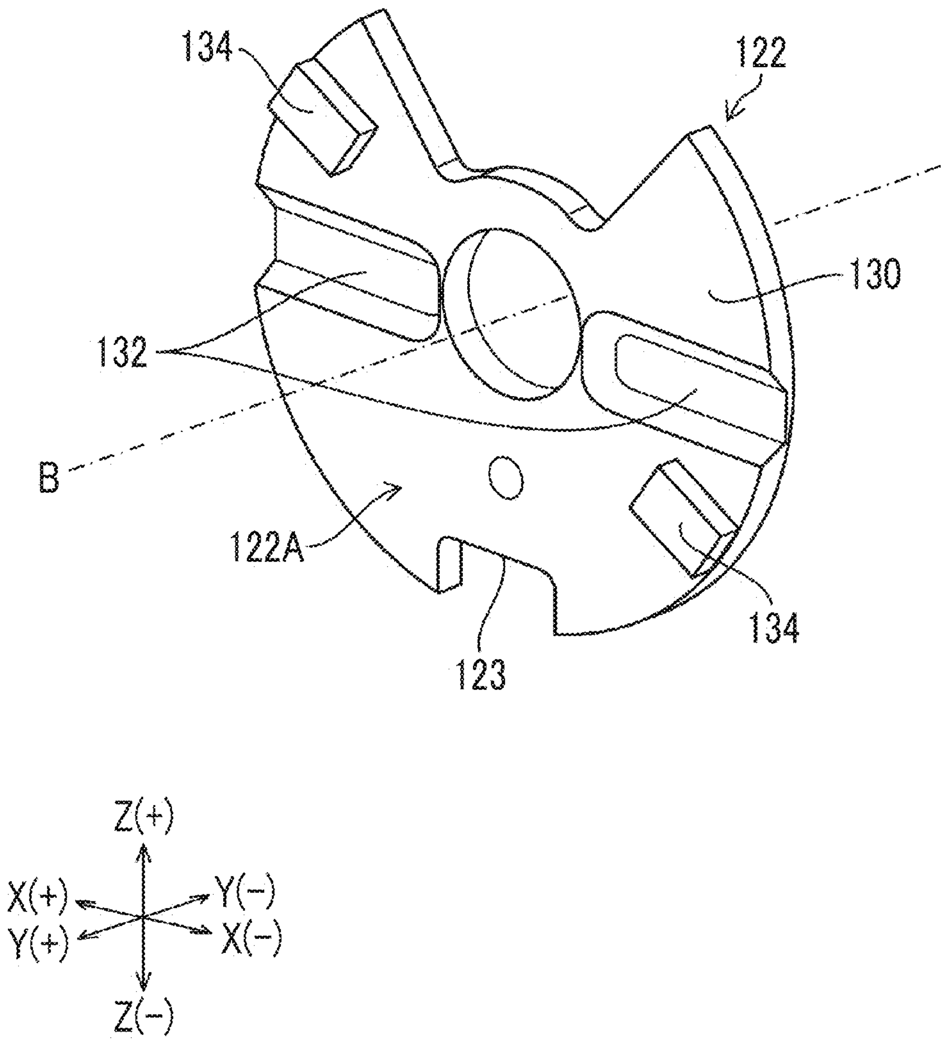
FIG. 8 is a perspective view of the switching plate as seen from a side to which a Y (+) direction extends.

FIG. 8 is a perspective view of the switching plate 122 and is a perspective view as seen from the side to which the Y (+) direction extends. As shown in FIG. 8, the switching plate 122 is formed in a disk-like shape. The front surface 122A of the switching plate 122 is a surface against which the abutting portion 118A of the rolling body 118 is pressed by the biasing force of the spring 116, and three abutting surfaces used to selectively switching the position of the plunger 104 between the three positions (the locking position, the non-locking position, and the lock position) are disposed at the front surface 122A. The vertical positions (the positions in the Y direction) of the three abutting surfaces are different from each other. Hereinafter, detailed description will be provided.

A locking abutting surface 130, a non-locking abutting surface 132, and a lock abutting surface 134, which are the three abutting surfaces, are disposed at the front surface 122A of the switching plate 122. In addition, on the front surface 122A, the locking abutting surface 130, the non-locking abutting surface 132, and the lock abutting surface 134 are disposed at different positions in a circumferential direction. With the switching plate 122 rotated in accordance with a switching operation (a rotating operation) performed on the operation ring 121 of the switching operation portion 26, an abutting surface disposed at a position facing the plunger 104 (specifically, the abutting portion 118A of the rolling body 118) can be switched between the three abutting surfaces (the locking abutting surface 130, the non-locking abutting surface 132, and the lock abutting surface 134) on the switching plate 122.

The locking abutting surface 130 is a surface that occupies a major portion of a region on the front surface 122A, and is formed in a planar shape along the XZ plane. The non-locking abutting surface 132 is formed as a concave surface recessed, toward the side to which the Y (−) direction extends, with respect to the locking abutting surface 130. The lock abutting surface 134 is formed as a convex surface that protrudes, to the side to which the Y (+) direction extends, with respect to the locking abutting surface 130. The locking abutting surface 130 and the non-locking abutting surface 132 are examples of a first abutting surface and a second abutting surface according to the embodiment of the present invention. In addition, the lock abutting surface 134 is an example of a third abutting surface of the embodiment of the present invention.

Figure 9A:
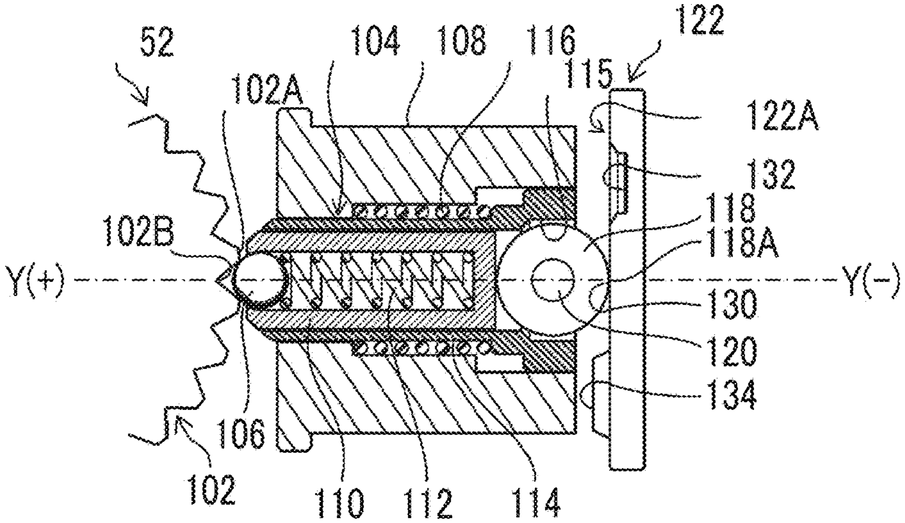
FIGS. 9A to 9C are explanatory views showing three positions of a plunger.
Figure 9B:
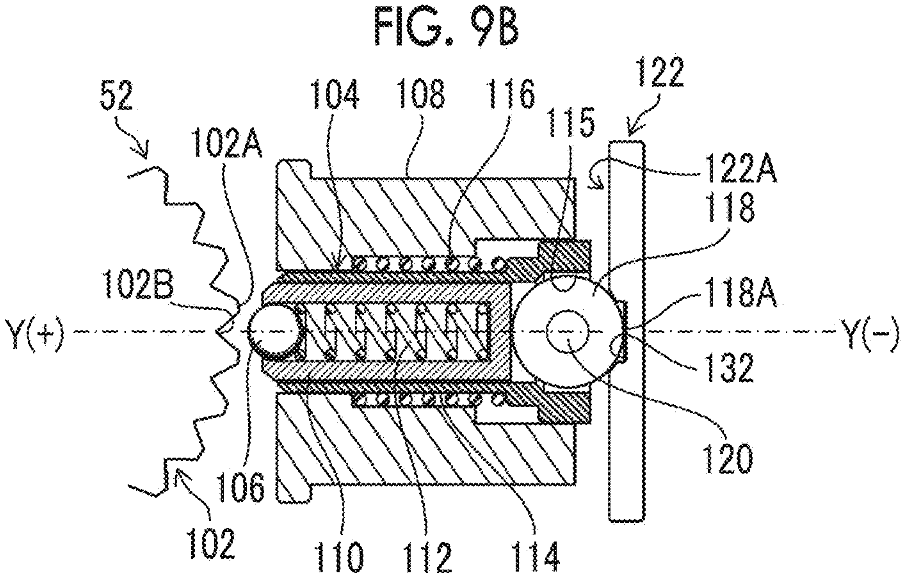
Figure 9C:
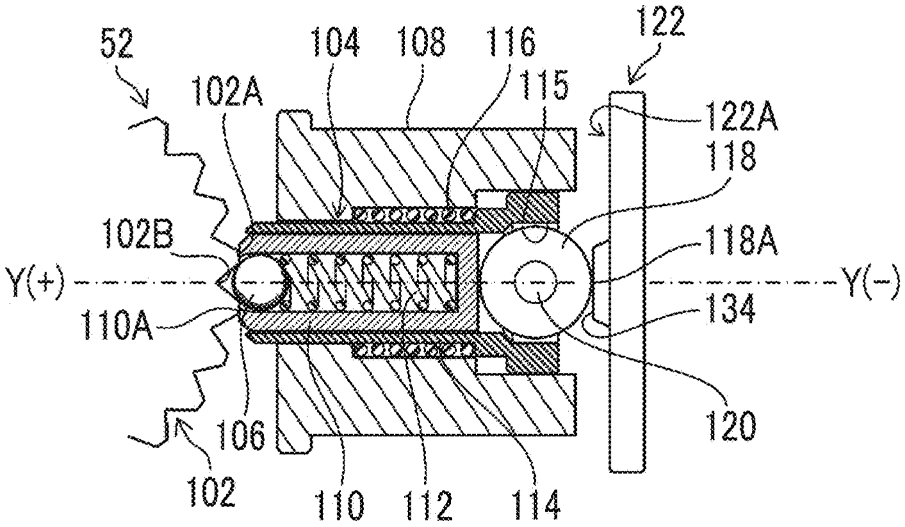

FIGS. 9A to 9C are explanatory views showing three positions of the plunger 104. FIGS. 9A to 9C show how switching between a latched state, a free state, and a locked state (which will be described later) is performed with the position of the plunger 104 changing in three stages in accordance with the rotational position of the switching plate 122.

First, as shown in FIG. 9A, in a case where the locking abutting surface 130 is positioned at a position facing the abutting portion 118A of the rolling body 118, the abutting portion 118A of the rolling body 118 abuts the locking abutting surface 130 against the biasing force of the spring 116. Accordingly, the plunger 104 is disposed at the locking position. In this case, since the locking abutting surface 130 is provided at a position where a distance (a distance in the Y direction) to the disk 52 is smaller than a distance between the non-locking abutting surface 132 and the disk 52, the plunger 104 disposed at the locking position is in a state of being closer to the disk 52 than the plunger 104 disposed at the non-locking position (which will be described later) is. In addition, in a case where the plunger 104 is disposed at the locking position, the locking portion 106 enters a state of being locked at the serrated portion 102. Hereinafter, such a state may be referred to as a "latched state".

In the latched state, the locking portion 106 is locked at the serrated portion 102 and thus the disk 52 and the sprocket 50 cannot be rotated in a state where a predetermined operation force (an operation torque) is not applied to the lateral bending lever 30. As a result, the bendable portion 18 can be fixed in a desired bent state.

Meanwhile, in the latched state, in a case where the lateral bending lever 30 is operated to be swung by an operation force equal to or greater than the predetermined operation force, the disk 52 and the sprocket 50 are rotationally driven, against the biasing force of the spring 112, in the same direction as a direction in which the lateral bending lever 30 is swung.

In a case where the disk 52 starts to rotate in the latched state, the locking portion 106 is moved, toward the side to which the Y (−) direction extends, from the tooth groove 102B side to the tooth tip 102A side against the biasing force of the spring 112. Then, in a case where the locking portion 106 climbs over the tooth tip 102A, the locking portion 106 is moved by the biasing force of the spring 116 toward the side to which the Y (+) direction extends and is locked at the serrated portion 102 again.

That is, the spring 112 has a biasing force that allows the locking portion 106 to climb over the tooth tip 102A in a case where the disk 52 is rotated in the latched state (a state where the plunger 104 has transitioned to the locking position).

Regarding the lateral bending lever 30, a latching operation (an operation in which clicking sounds like "tick-tock" are generated) of repeatedly stopping and swinging for every pitch of the unevenness portions (the tooth tips 102A and the tooth grooves 102B) can be performed since the spring 112 has such a biasing force. As a result, the bendable portion 18 is operated to be bent at each angle corresponding to the above-described pitch and is fixed in a bent state at that time. Note that the spring 112 corresponds to a first biasing member according to the embodiment of the present invention.

Next, as shown in FIG. 9B, in a case where the non-locking abutting surface 132 is positioned at a position facing the abutting portion 118A of the rolling body 118, the abutting portion 118A of the rolling body 118 of the plunger 104 abuts the non-locking abutting surface 132 against the biasing force of the spring 116. Accordingly, the plunger 104 is disposed at the non-locking position. In this case, since the non-locking abutting surface 132 is provided at a position where a distance (a distance in the Y direction) to the disk 52 is larger than a distance between the locking abutting surface 130 and the disk 52, the plunger 104 disposed at the non-locking position is in a state of being more distant from the disk 52 than the plunger 104 disposed at the locking position is. In addition, in a case where the plunger 104 is disposed at the non-locking position, the locking portion 106 enters a state of being withdrawn from the serrated portion 102. Hereinafter, such a state may be referred to as a "free state".

In the free state, since the locking portion 106 is withdrawn to the side to which the Y (−) direction extends with respect to the serrated portion 102 and is not locked at the serrated portion 102, the disk 52 and the sprocket 50 can be rotated freely. Accordingly, the lateral bending lever 30 enters a state where the bendable portion 18 can be continuously bent. Note that the spring 116 is an example of a second biasing member according to the embodiment of the present invention.

Next, as shown in FIG. 9C, in a case where the lock abutting surface 134 is positioned at a position facing the abutting portion 118A of the rolling body 118, the abutting portion 118A of the rolling body 118 of the plunger 104 abuts the lock abutting surface 134 against the biasing force of the spring 116. Accordingly, the plunger 104 is disposed at the lock position. In this case, since the lock abutting surface 134 is provided at a position where a distance (a distance in the Y direction) to the disk 52 is smaller than a distance between the locking abutting surface 130 and the disk 52, the plunger 104 disposed at the lock position is in a state of being closer to the disk 52 than the plunger 104 disposed at the locking position is. In addition, in a case where the plunger 104 is disposed at the lock position, a distal end portion 110A of the locking pin 110 is in a state of being pressed against the serrated portion 102. Hereinafter, such a state may be referred to as a "locked state".

In the locked state, since the locking portion 106 is pressed against the serrated portion 102 by a force greater than the biasing force of the spring 112 and the distal end portion 110A of the locking pin 110 is pressed against the serrated portion 102, the disk 52 and the sprocket 50 are made completely unable to rotate. Accordingly, the lateral bending lever 30 enters the locked state in which a bending operation cannot be performed. In this case, the bendable portion 18 is reliably fixed in a desired bent state.

In addition, regarding the switching plate 122 of the present example, a pair of the non-locking abutting surfaces 132 and a pair of the lock abutting surfaces 134 are disposed to correspond to a pair of the plungers 104 (refer to FIG. 8). The pair of non-locking abutting surfaces 132 and the pair of lock abutting surfaces 134 are disposed at positions that are 180 degrees offset from each other in a circumferential direction of the switching plate 122.

In a case where the switching plate 122 configured as described above is rotationally driven by the switching operation portion 26, the rolling bodies 118 of the pair of plungers 104 simultaneously abut the locking abutting surface 130 at a first rotational position, simultaneously abut the pair of non-locking abutting surfaces 132 at a second rotational position different from the first rotational position, and simultaneously abut the pair of lock abutting surfaces 134 at a third rotational position different from the first and second rotational positions. Accordingly, the pair of plungers 104 simultaneously and selectively switches between the locking positions, the non-locking positions, and the lock positions. As a result, the lateral bending lever 30 and the vertical bending lever 32 simultaneously and selectively switch between the latched state, the free state, and the locked state. Note that since the locking abutting surface 130 occupies the major portion of the front surface 122A, it is not necessary that a pair of the locking abutting surfaces 130 is disposed as with the non-locking abutting surfaces 132 and the lock abutting surfaces 134.

Example of Use of Ultrasound Probe 10

Next, one of examples of use of the ultrasound probe 10 configured as described above will be described.

First, an operator grips the grip portion 28 of the operation portion 12 of the ultrasound probe 10 and inserts the insertion portion 14 into a subject via, for example, a trocar. In this case, the switching operation portion 26 is rotated around the longitudinal axis B so that the pair of plungers 104 transitions to the non-locking positions (the free state) in advance. Accordingly, a state where a swinging operation of the lateral bending lever 30 and the vertical bending lever 32 is performed freely (continuously) is achieved.

Thereafter, the operator performs the swinging operation of the lateral bending lever 30 and the vertical bending lever 32 as appropriate such that the bendable portion 18 of the insertion portion 14 is bent in the lateral direction (the X direction) and the vertical direction (the Z direction) and thus the ultrasonic wave emission surface 20A of the probe 20 is brought into contact with or close to a surface of an imaging target portion (an organ (for example, a liver)).

Next, in order to fix a bent state of the bendable portion 18, the operator rotates the operation ring 121 around the longitudinal axis B by using the thumb of a hand gripping the grip portion 28 such that the switching plate 122 is rotated and the pair of plungers 104 transitions to the locking positions (the latched state) or the lock positions (the locked state). Accordingly, the bendable portion 18 can be fixed in a desired bent state.

Note that in a case where the pair of plungers 104 is caused to transition to the locking positions by means of the switching operation portion 26, it is possible to perform a latching operation by using the lateral bending lever 30 and the vertical bending lever 32. In addition, in a case where the pair of plungers 104 is caused to transition to the lock positions by means of the switching operation portion 26, it is completely not possible to swing the lateral bending lever 30 and the vertical bending lever 32. In this case, even in a case where a force is applied to the lateral bending lever 30 and the vertical bending lever 32 inadvertently, the lateral bending lever 30 and the vertical bending lever 32 do not move.

Next, a drive signal is supplied from a transmission unit of the ultrasound imaging apparatus to the probe 20 and ultrasonic waves are sent from the probe 20 to the imaging target portion. Ultrasonic waves generated from the imaging target portion are received by the probe 20 as a reflection echo signal. A reflection echo signal output from the probe 20 is subjected to processing such as amplification by a reception unit of the ultrasound imaging apparatus and then is subjected to image processing by an image processing unit of the ultrasound imaging apparatus. Thereafter, an ultrasound image is displayed by a display unit. While referring to the displayed ultrasound image, for example, another operator inserts a biopsy needle into a body cavity and extracts the tissue of the imaging target portion.

Thereafter, in order to unfix a bent state of the bendable portion 18, the operator operating the ultrasound probe 10 rotates (rotationally drives the switching plate 122) the switching operation portion 26 around the longitudinal axis B by using the thumb of a hand gripping the grip portion 28 such that the pair of plungers 104 transitions to the non-locking positions. Accordingly, a state where a swinging operation of the lateral bending lever 30 and the vertical bending lever 32 is performed freely is achieved. Thereafter, the lateral bending lever 30 and the vertical bending lever 32 are swung such that the bendable portion 18 returns to, for example, a straight state and then the insertion portion 14 is pulled out from the subject. The example described above is one of examples of use of the ultrasound probe 10.

As described above, in the case of the ultrasound probe 10 of the embodiment, the front surface 122A of the switching plate 122 which integrally rotates with the switching operation portion 26 is provided with at least two abutting surfaces (the locking abutting surface 130 and the non-locking abutting surface 132) that are different from each other in height position (position in the Y direction). In addition, it is possible to selectively switch the state of the bending levers (the lateral bending lever 30 and the vertical bending lever 32) between two states (the latched state and the free state) by rotating the switching operation portion 26 so that the switching plate 122 is rotated and a positional relationship between the two abutting surfaces and the plunger 104 is changed and switching the position of the plunger 104, which abuts the two abutting surfaces due to the biasing force of the spring 116, between two positions (the locking position and the non-locking position). Accordingly, it is possible to improve usability in relation to a fixing operation and an unfixing operation of the bendable portion 18.

In addition, in the embodiment, the front surface 122A of the switching plate 122 is provided with the lock abutting surface 134 in addition to the above-described two abutting surfaces. In addition, it is possible to switch the state of the bending levers (the lateral bending lever 30 and the vertical bending lever 32) to the locked state by rotating the switching operation portion 26 so that the switching plate 122 is rotated and switching the position of the plunger 104, which abuts the lock abutting surface 134 due to the biasing force of the spring 116, to the lock position. Accordingly, it is possible to further improve usability in relation to a fixing operation and an unfixing operation of the bendable portion 18.

MODIFICATION EXAMPLES

Hereinafter, some of modification examples will be described.

First Modification Example

In the embodiment, an aspect in which three abutting surfaces (the locking abutting surface 130, the non-locking abutting surface 132, and the lock abutting surface 134) are disposed at the front surface 122A of the switching plate 122 has been described. However, the present invention is not limited thereto. For example, as in the case of a switching plate 140 and the case of a switching plate 150 in other aspects shown in FIGS. 10 and 11, an aspect in which only the locking abutting surface 130 and the non-locking abutting surface 132 out of the three abutting surfaces are disposed may also be adopted.

Figure 10:
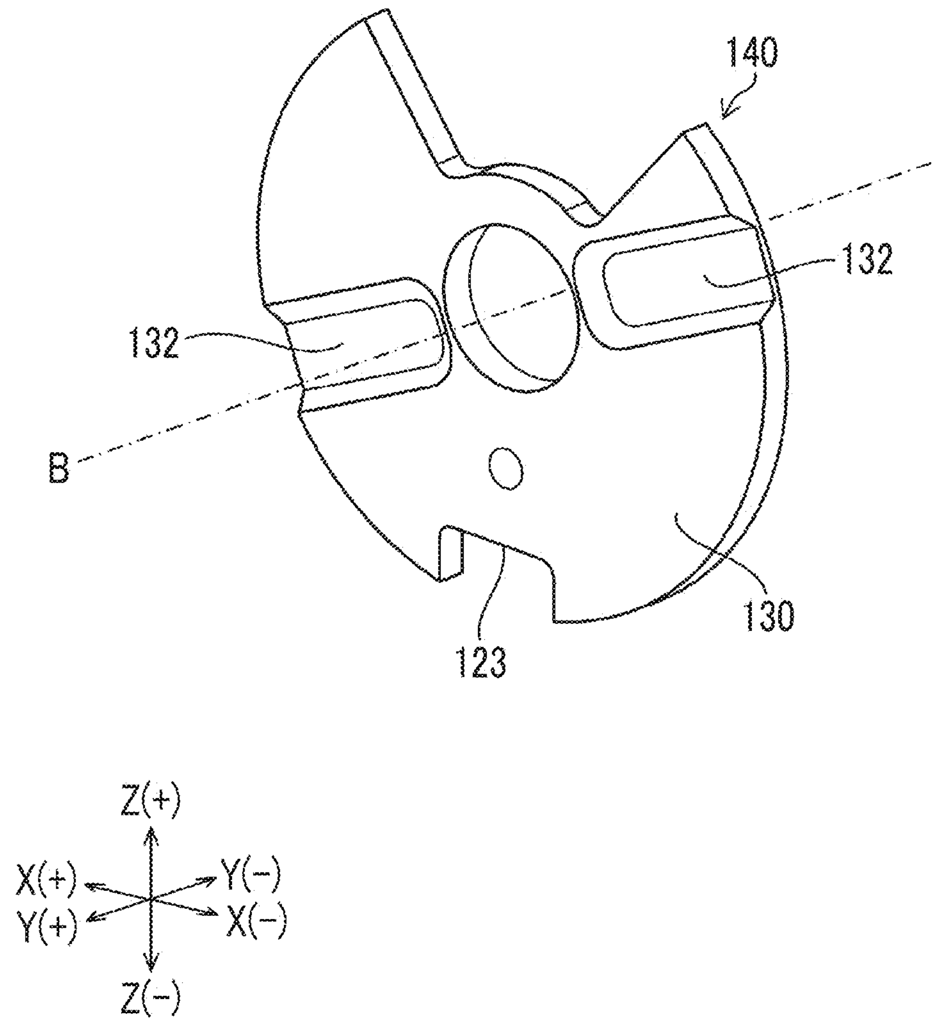
FIG. 10 is a perspective view showing a configuration of a switching plate of another aspect.

Regarding the switching plate 140 shown in FIG. 10, the paired non-locking abutting surfaces 132 are disposed at positions that are 180 degrees offset from each other in a circumferential direction of the switching plate 122 and are disposed at positions that are offset from the paired non-locking abutting surfaces 132 shown in FIG. 8 in the circumferential direction of the switching plate 122.

Figure 12A:
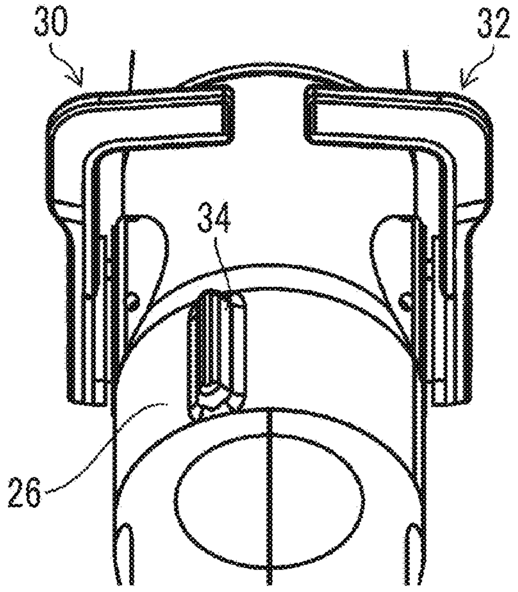
FIGS. 12A and 12B are explanatory views showing an operation example of a switching operation portion.

In the case of the switching plate 140, in a case where the switching operation portion 26 is rotated to a position shown in FIG. 12A, a pair of the rolling bodies 118 abuts the pair of non-locking abutting surfaces 132 respectively and each of the pair of plungers 104 is positioned at the non-locking position. Accordingly, both of the lateral bending lever 30 and the vertical bending lever 32 enter the free state.

Figure 12B:
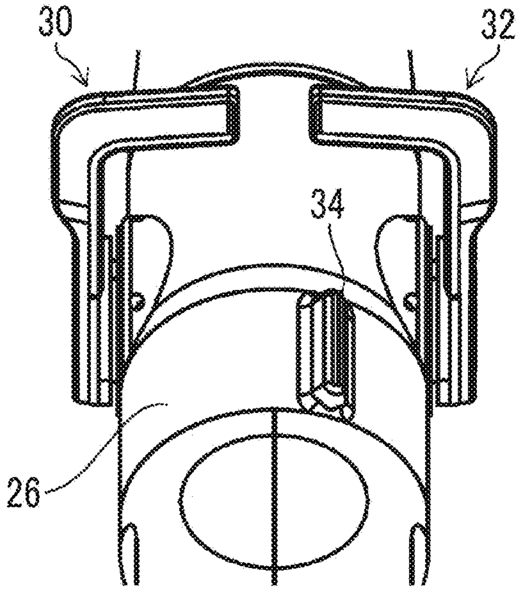

In addition, in a case where the switching operation portion 26 is rotated to a position shown in FIG. 12B, each of the pair of rolling bodies 118 abuts the locking abutting surface 130 and each of the pair of plungers 104 is positioned at the locking position. Accordingly, both of the lateral bending lever 30 and the vertical bending lever 32 enter the latched state.

Figure 11:
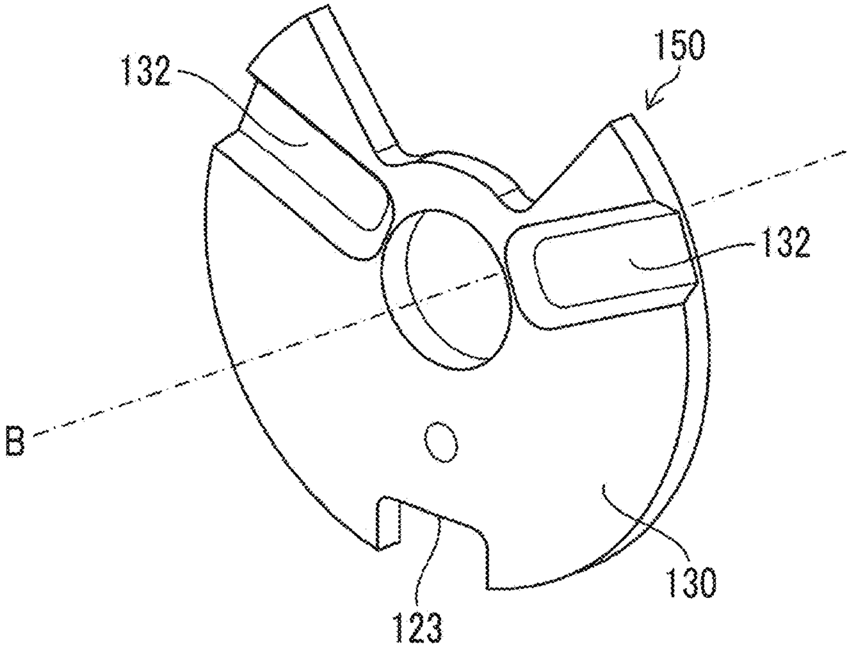
FIG. 11 is a perspective view showing a configuration of a switching plate of another aspect.
Figure 11:
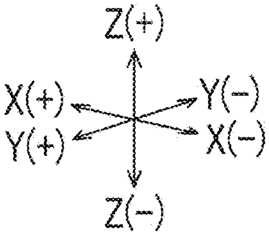

Meanwhile, regarding the switching plate 150 shown in FIG. 11, the paired non-locking abutting surfaces 132 are disposed at positions that are closer to each other than positions that are 180 degrees offset from each other in the circumferential direction of the switching plate 122 are.

In the case of the switching plate 150, in a case where the switching operation portion 26 is rotated to a position shown in FIG. 12A, the rolling body 118 on the lock mechanism 100 side abuts the non-locking abutting surface 132 and the rolling body 118 on the lock mechanism 200 side abuts the locking abutting surface 130. Accordingly, the plunger 104 on the lock mechanism 100 side is positioned at the non-locking position and the plunger 104 on the lock mechanism 200 side is positioned at the locking position, so that the lateral bending lever 30 enters the free state and the vertical bending lever 32 enters the latched state.

In addition, in a case where the switching operation portion 26 is rotated to a position shown in FIG. 12B, the rolling body 118 on the lock mechanism 100 side abuts the locking abutting surface 130 and the rolling body 118 on the lock mechanism 200 side abuts the non-locking abutting surface 132. Accordingly, the plunger 104 on the lock mechanism 100 side is positioned at the locking position and the plunger 104 on the lock mechanism 200 side is positioned at the non-locking position, so that the lateral bending lever 30 enters the latched state and the vertical bending lever 32 enters the free state.

As described above, it is possible for the switching operation portion 26 to selectively switch the position of at least one of the paired plungers 104 between the locking position and the non-locking position by changing positions where the locking abutting surface 130 and the non-locking abutting surfaces 132 are disposed at the switching plate 122.

Note that although the above-described aspects shown in FIGS. 10 and 11 are aspects in which the two abutting surfaces (the locking abutting surface 130 and the non-locking abutting surface 132) are disposed, from the viewpoint of reliably fixing the bendable portion 18 in a bent state, it is preferable that the lock abutting surface 134 is also disposed as in the case of the embodiment.

Second Modification Example

Figure 13:
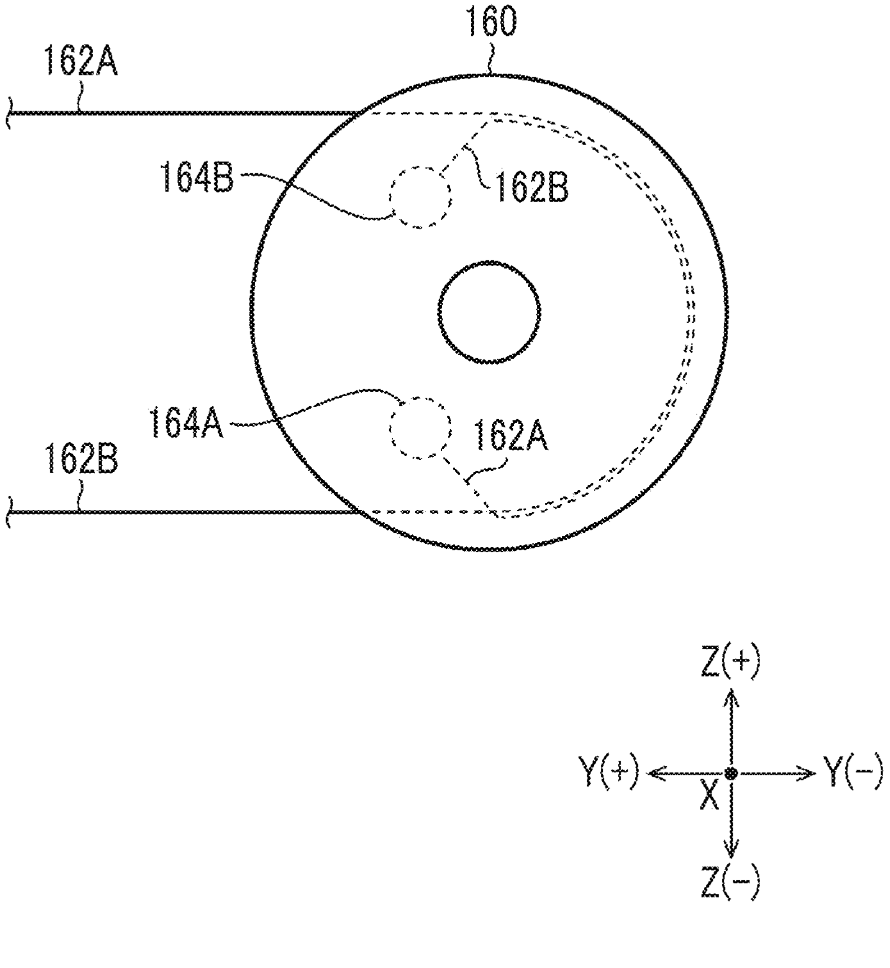
FIG. 13 is a schematic explanatory view related to a case where a pulley is adopted as a rotary driving body.

In the embodiment, an aspect in which the sprockets 50 and 70 are adopted as rotary driving bodies has been described. However, the present invention is not limited thereto. For example, a pulley 160 shown in FIG. 13 may be adopted instead of the sprockets 50 and 70. In a case where the pulley 160 is employed, linear members 162A and 162B such as two wires may be wound around the pulley 160 and bending operation wires may be respectively connected to end portions of the linear members 162A and 162B. Note that locking members 164A and 164B are respectively attached to end portions of the linear members 162A and 162B that are on the pulley 160 side. The locking members 164A and 164B are locked in locking holes (not shown) formed in the pulley 160 so that the linear members 162A and 162B are connected to the pulley 160.

Third Modification Example

Figure 14:
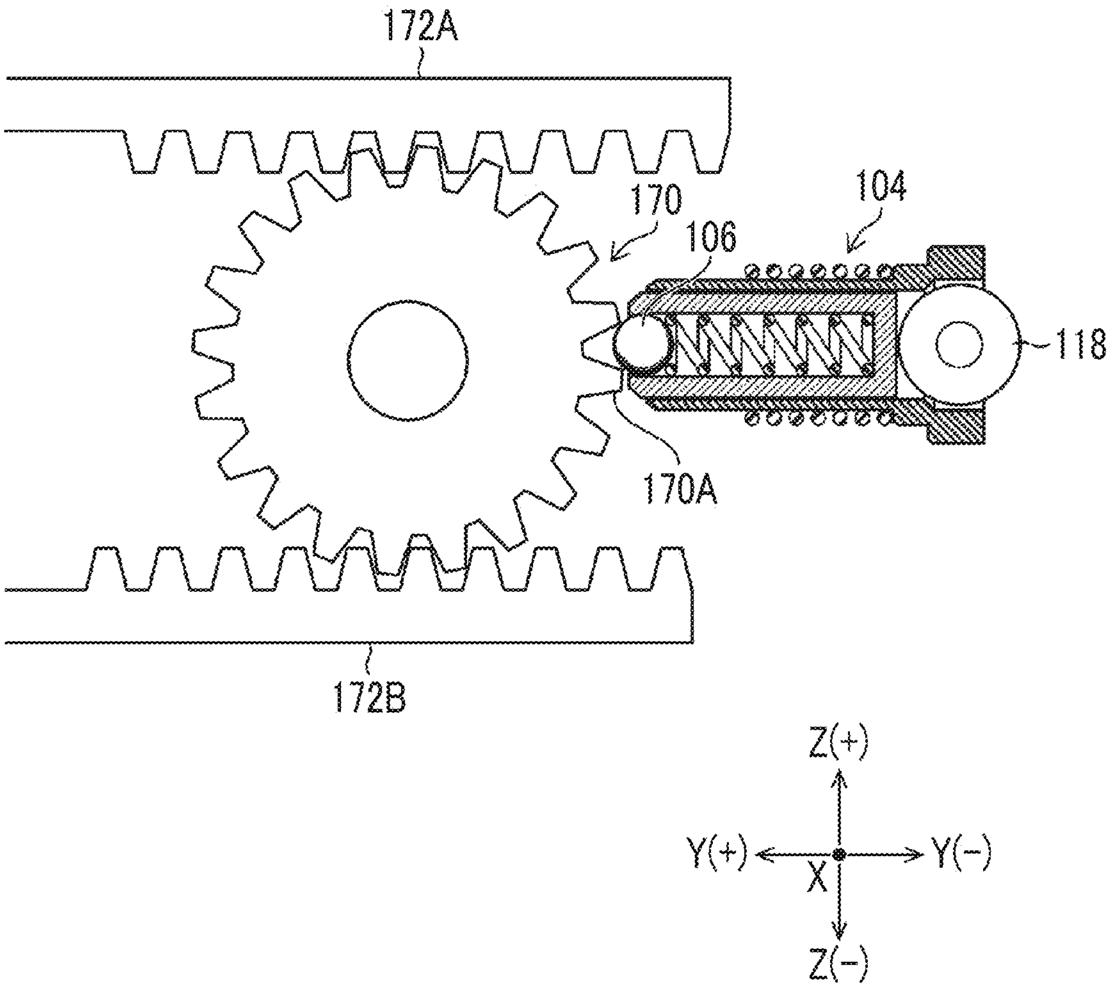
FIG. 14 is a schematic explanatory view related to a case where a pinion is adopted as the rotary driving body.

In addition, a pinion 170 shown in FIG. 14 may be adopted as a rotary driving body. In a case where the pinion 170 is adopted, bending operation wires may be respectively connected to end portions of a pair of racks 172A and 172B meshing with teeth 170A which are provided at an outer peripheral surface of the pinion 170. In addition, in a case where the pinion 170 is adopted, the teeth 170A of the pinion

170 can also be used as unevenness portions at which the locking portion 106 is locked. As a result, the rotary driving body and a rotary member can be integrated with each other since the pinion 170 is adopted.

Fourth Modification Example

In the embodiment, the serrated portion 102 at which the tooth tips 102A and the tooth grooves 102B are formed at constant pitches as unevenness portions provided at an outer peripheral surface of a rotary member has been described as an example. However, the present invention is not limited thereto. For example, unevenness portions of which recess portions and protrusion portions are formed at constant pitches may also be adopted. Note that from the viewpoint of performing a regular latching operation, it is preferable that the pitch of the unevenness portions is constant.

Fifth Modification Example

In the embodiment, the pair of bending operation members (the lateral bending lever 30 and the vertical bending lever 32) has been described as an example of bending operation members. However, the present invention is not limited thereto. For example, a configuration in which only one of the lateral bending lever 30 and the vertical bending lever 32 is provided may also be adopted.

Sixth Modification Example

In the embodiment, the ball-shaped locking portion 106 has been described as an example of a locking portion. However, the present invention is not limited thereto. For example, the shape of the locking portion may be a columnar shape and the shape of an outer surface as seen in the X direction may be an arc-like shape corresponding to the shapes of the tooth grooves 102B of the serrated portion 102.

In the embodiment, a configuration in which recess portions and protrusion portions are formed at the front surface 122A of the switching plate 122 so that the abutting surfaces (the locking abutting surface 130, the non-locking abutting surface 132, and the lock abutting surface 134) are disposed has been described as an example. However, the present invention is not limited thereto. For example, the front surface 122A of the switching plate 122 may not be provided with recess portions while being provided with two protrusion portions that are different from each other in height position (position in the Y direction) so that the abutting surfaces are disposed. In addition, the front surface 122A of the switching plate 122 may not be provided with protrusion portions while being provided with two recess portions that are different from each other in height position (position in the Y direction) so that the abutting surfaces are disposed.

Seventh Modification Example

In the embodiment, the ultrasound probe 10 has been described as an example of a target to which a medical appliance according to the embodiment of the present invention is applied. However, the present invention is not limited to the ultrasound probe 10 and can be applied to various medical appliances. That is, the present invention can be applied to, for example, a laparoscope and an endoscope including a soft insertion portion as long as the target of application is a medical appliance of which an insertion portion includes a bendable portion.

Although a medical appliance according to the embodiment of the present invention has been described above, the present invention may be improved or modified in some ways without departing from the gist of the present invention.

EXPLANATION OF REFERENCES

10: ultrasound probe
12: operation portion
14: insertion portion
16: insertion portion main body
18: bendable portion
20: probe
20A: ultrasonic wave emission surface
22: connecting portion
24: lever attachment portion
26: switching operation portion
27: protrusion portion
28: grip portion
30: lateral bending lever
30A: upper end portion
30B: circular base portion
32: vertical bending lever
32A: upper end portion
32B: circular base portion
34: finger hook portion
40: tubular body
40A: base end opening portion
42: operation region
44: operation region
46: shaft supporting portion
48: shaft
48A: one end portion
48B: other end portion
50: sprocket
50A: bearing hole
50B: facing surface
52: disk
52A: bearing hole
52B: facing surface
54: arc-shaped recess portion
56: arc-shaped protrusion portion
58: protrusion portion
60: hole portion
62: chain
62A: one end portion
62B: other end portion
64A: connection tool
64B: connection tool
66A: wire
66B: wire
70: sprocket
70A: bearing hole
72: disk
72A: bearing hole
78: protrusion portion
80: hole portion
82: chain
82A: one end portion
82B: other end portion
84A: connection tool
84B: connection tool
86A: wire
86B: wire
100: lock mechanism
102: serrated portion 102A: tooth tip
102B: tooth groove
104: plunger
106: locking portion
108: plunger supporting portion
108A: screw hole
110: locking pin
111: spring accommodation groove
110A: distal end portion
112: spring
114: sleeve
115: base end opening portion
115A: base end surface
116: spring
118: rolling body
118A: abutting portion
120: shaft
121: operation ring
122: switching plate
122A: front surface
122B: bearing hole
123: recess portion
124: bush
126: bolt
130: locking abutting surface
132: non-locking abutting surface
134: lock abutting surface
140: switching plate
150: switching plate
160: pulley
162A: linear member
162B: linear member
164A: locking member
164B: locking member
170: pinion
170A: tooth
172A: rack
172B: rack
200: lock mechanism
A: longitudinal axis
B: longitudinal axis

What is claimed is:

1. A medical appliance comprising:

an insertion portion that includes a bendable portion that is bendable;

an operation portion that is connected to a base end side of the insertion portion and that includes a bending operation member;

a rotary driving body that is disposed in the operation portion and is rotationally driven by the bending operation member;

a bending operation wire that is inserted into the insertion portion and the operation portion and that bends the bendable portion by moving forward and backward in accordance with movement of the rotary driving body;

a rotary member that is integrally rotatable with the rotary driving body and of which an outer peripheral surface is provided with an unevenness portion;

a locking portion main body that includes a locking portion lockable at the unevenness portion and that is transitionable between a locking position where the locking portion is locked at the unevenness portion and a non-locking position where the locking portion is not locked at the unevenness portion; and a switching operation portion that is provided to be rotatable around a longitudinal axis of the operation portion and that causes the locking portion main body to selectively switch between the locking position and the non-locking position, wherein the switching operation portion includes a switching plate that rotates around the longitudinal axis, the switching plate includes a first abutting surface and a second abutting surface that are disposed at different positions in a circumferential direction on a surface of the switching plate that is on a rotary member side, the first abutting surface is provided at a position where a distance to the rotary member is smaller than a distance between the second abutting surface and the rotary member, the locking portion main body is disposed at the locking position in a case where the locking portion main body abuts the first abutting surface and is disposed at the non-locking position in a case where the locking portion main body abuts the second abutting surface, the switching plate includes a third abutting surface that is disposed at a position different from positions of the first abutting surface and the second abutting surface in the circumferential direction on the surface of the switching plate that is on the rotary member side, the third abutting surface is provided at a position where a distance to the rotary member is smaller than a distance between the first abutting surface and the rotary member, and the rotary member enters a state of being not rotatable in a case where the locking portion main body abuts the third abutting surface.

2. The medical appliance according to claim 1, wherein the locking portion main body includes the locking portion that is provided on the rotary member side and that has a ball-like shape, and a first biasing member that biases the locking portion toward the rotary member side.

3. The medical appliance according to claim 2, wherein the locking portion main body includes a second biasing member that biases the locking portion main body toward a switching plate side.

4. The medical appliance according to claim 3, wherein the locking portion main body includes a roll body that rotates with the roll body being in contact with the surface of the switching plate that is on the rotary member side.

5. The medical appliance according to claim 2, wherein the first biasing member has a biasing force that allows the locking portion to climb over the unevenness portion in a case where the rotary member rotates in a state where the locking portion main body is positioned at the locking position.

6. The medical appliance according to claim 1, wherein the rotary driving body is a sprocket.

7. The medical appliance according to claim 1, wherein the rotary driving body is a pulley.

8. The medical appliance according to claim 1, wherein the rotary driving body is a pinion.

9. The medical appliance according to claim 1, wherein the rotary driving body and the rotary member are integrated with each other.

10. The medical appliance according to claim 1, wherein the unevenness portions are provided at constant pitches at the outer peripheral surface of the rotary member.

11. The medical appliance according to claim 1, wherein a pair of the rotary driving bodies, a pair of the rotary members, and a pair of the locking portion main bodies are provided, and the switching operation portion causes at least one of the pair of locking portion main bodies to selectively switch between the locking position and the non-locking position.

* * * * *